(12) United States Patent
Raja et al.

(10) Patent No.: US 10,429,256 B2
(45) Date of Patent: Oct. 1, 2019

(54) MECHANISMS OF LOCAL STRESS SENSING IN MULTIFUNCTIONAL POLYMER FILMS USING FLUORESCENT TETRAPOD NANOCRYSTALS

(71) Applicants: Shilpa N. Raja, Berkeley, CA (US); Danylo Zherebetskyy, Walnut Creek, CA (US); Siva Wu, Berkeley, CA (US); Peter Ercius, Oakland, CA (US); Andrew C. K. Olson, San Francisco, CA (US); Paul Alvisatos, Berkeley, CA (US); Robert O. Ritchie, Berkeley, CA (US); Sanjay Govindjee, Lafayette, CA (US)

(72) Inventors: Shilpa N. Raja, Berkeley, CA (US); Danylo Zherebetskyy, Walnut Creek, CA (US); Siva Wu, Berkeley, CA (US); Peter Ercius, Oakland, CA (US); Andrew C. K. Olson, San Francisco, CA (US); Paul Alvisatos, Berkeley, CA (US); Robert O. Ritchie, Berkeley, CA (US); Sanjay Govindjee, Lafayette, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 15/607,158

(22) Filed: May 26, 2017

(65) Prior Publication Data

US 2018/0045590 A1 Feb. 15, 2018

Related U.S. Application Data

(60) Provisional application No. 62/342,653, filed on May 27, 2016.

(51) Int. Cl.
*G01L 1/24* (2006.01)
*C08J 5/18* (2006.01)
(Continued)

(52) U.S. Cl.
CPC ............. *G01L 1/247* (2013.01); *C08J 5/18* (2013.01); *C08K 3/10* (2013.01); *C08K 3/30* (2013.01);
(Continued)

(58) Field of Classification Search
CPC ........... C08J 5/18; C08J 2353/00; C08K 3/10; C08K 3/30; C08K 7/16; C08K 9/02;
(Continued)

(56) References Cited

U.S. PATENT DOCUMENTS

2012/0211670 A1* 8/2012 Choi ............... B82Y 15/00
250/459.1

OTHER PUBLICATIONS

Talapin et al., "Seeded growth of highly luminescent CdSe/CdS nanoheterostructures with rod and tetrapod morphologies," Nano Lett., 7(10), pp. 2951-2959. (Year: 2007).*

(Continued)

*Primary Examiner* — Josephine L Chang

(57) ABSTRACT

Nanoscale stress-sensing can be used across fields ranging from detection of incipient cracks in structural mechanics to monitoring forces in biological tissues. We demonstrate how tetrapod quantum dots (tQDs) embedded in block-copolymers act as sensors of tensile/compressive stress. Remarkably, tQDs can detect their own composite dispersion and mechanical properties, with a switch in optomechanical response when tQDs are in direct contact. Using experimental characterizations, atomistic simulations and finite-element analyses, we show that under tensile stress, densely-packed tQDs exhibit a photoluminescence peak shifted to higher energies ("blue-shift") due to volumetric compressive (Continued)

stress in their core; loosely-packed tQDs exhibit a peak shifted to lower energies ("red-shift") from tensile stress in the core. The stress-shifts result from the tQD's unique branched morphology in which the CdS arms act as antennas that amplify the stress in the CdSe core. Our nanocomposites exhibit excellent cyclability and scalability with no degraded properties of the host polymer. Colloidal tQDs allow sensing in many materials to potentially enable auto-responsive, smart structural nanocomposites that self-predict impending fracture.

20 Claims, 10 Drawing Sheets

(51) Int. Cl.
| | |
|---|---|
| C08K 3/30 | (2006.01) |
| C08K 3/10 | (2018.01) |
| C09K 11/02 | (2006.01) |
| C09K 11/88 | (2006.01) |
| C09K 11/56 | (2006.01) |
| G01N 33/44 | (2006.01) |
| C08K 7/16 | (2006.01) |
| G01N 21/64 | (2006.01) |
| C08K 9/02 | (2006.01) |
| G01N 33/00 | (2006.01) |

(52) U.S. Cl.
CPC ............ *C08K 7/16* (2013.01); *C08K 9/02* (2013.01); *C09K 11/02* (2013.01); *C09K 11/565* (2013.01); *C09K 11/88* (2013.01); *G01N 21/6428* (2013.01); *G01N 21/6489* (2013.01); *G01N 33/442* (2013.01); *C08J 2353/00* (2013.01); *C08K 2003/3027* (2013.01); *C08K 2003/3036* (2013.01); *C08K 2201/001* (2013.01); *C08K 2201/003* (2013.01); *C08K 2201/011* (2013.01); *G01N 2033/0096* (2013.01)

(58) Field of Classification Search
CPC .... C08K 2003/3027; C08K 2003/3036; C08K 2201/001; C08K 2201/003; C08K 2201/011; C08K 3/18; C09K 11/02; C09K 11/565; C09K 11/88; G01N 21/6428; G01N 21/6489; G01N 33/442; G01N 2033/0096; G01L 1/247
USPC ........................................................ 524/420
See application file for complete search history.

(56) References Cited

OTHER PUBLICATIONS

Raja et al., "Influence of three-dimensional nanoparticle branching on the Young's modulus of nanocomposites: Effect of interface orientation," PNAS, 112(21), Supporting Information (SI). (Year: 2015).*
Raja et. al., "Mechanisms of Local Stress Sensing in Multifunctional Polymer Films Using Fluorescent Tetrapod Nanocrystals." Nano Letters, vol. 16, pp. 5060-5067, Jul. 13, 2016.
Gupta et. al., "Entropy-driven segregation of nanoparticles to cracks in multilayered composite polymer structures." Nature Materials, vol. 5, No. 3, pp. 229-233, Feb. 12, 2006.
Raja et. al., "Tetrapod Nanocrystals as Fluorescent Stress Probes of Electrospun Nanocomposites." Nano Letters, vol. 13, No. 8, pp. 3915-3922, Jul. 1, 2013.
Raja et. al., "Influence of three-dimensional nanoparticle branching on the Young's modulus of nanocomposites: Effect of interface orientation." Proceedings of the National Academy of Sciences United States of America, vol. 112, No. 21, pp. 6533-6538, May 2015.
Talapin et. al., "Prospects of Colloidal Nanocrystals for Electronic and Optoelectronic Applications." Chemical Reviews, vol. 110, No. 1, pp. 389-458, 2010.
Choi et. al., "From Artificial Atoms to Nanocrystal Molecules: Preparation and Properties of More Complex Nanostructures." Annual Review of Physical Chemistry, vol. 61, No. 1, pp. 369-389, May 5, 2010.
Wu et. al., "Self-healing polymeric materials: A review of recent developments." Progress in Polymer Science, vol. 33, No. 5, pp. 479-522, May 2008.
Schrier et. al., "Mechanical and Electronic-Structure Properties of Compressed CdSe Tetrapod Nanocrystals ." Journal of Nanoscience and Nanotechnology, vol. 8, No. 4, pp. 1994-1998, Apr. 2008.
Choi et. al., "Strain-Dependent Photoluminescence Behavior of CdSe/CdS Nanocrystals with Spherical, Linear, and Branched Topologies." Nano Letters, vol. 9, No. 10, pp. 3544-3549, Aug. 13, 2009.
Fang et. al., "Mechanical and electrical properties of CdTe tetrapods studied by atomic force microscopy ." The Journal of Chemical Physics, vol. 127, No. 18, pp. 184704-1 184704-6, Nov. 2007.
Choi et. al., "Spatially Indirect Emission in a Luminescent Nanocrystal Molecule." Nano Letters, vol. 11, No. 6, pp. 2358-2362, May 19, 2011.
Bockstaller et. al., "Block Copolymer Nanocomposites: Perspectives for Tailored Functional Materials." Advanced Materials, vol. 17, No. 11, pp. 1331-1349, May 24, 2005.
Balazs et. al., "Nanoparticle Polymer Composites: Where Two Small Worlds Meet." Science, vol. 314, No. 5802, pp. 1107-1110, Nov. 17, 2006.
Raja et al., "Microscopic mechanisms of deformation transfer in high dynamic range branched nanoparticle deformation sensors," Nature Communications (2018) 9:1155.
Choi, C.L., et al., "Luminescent nanocrystal stress gauge." Proceedings of the National Academy of Sciences, vol. 107, No. 50, 21306-21310, 2010.

* cited by examiner

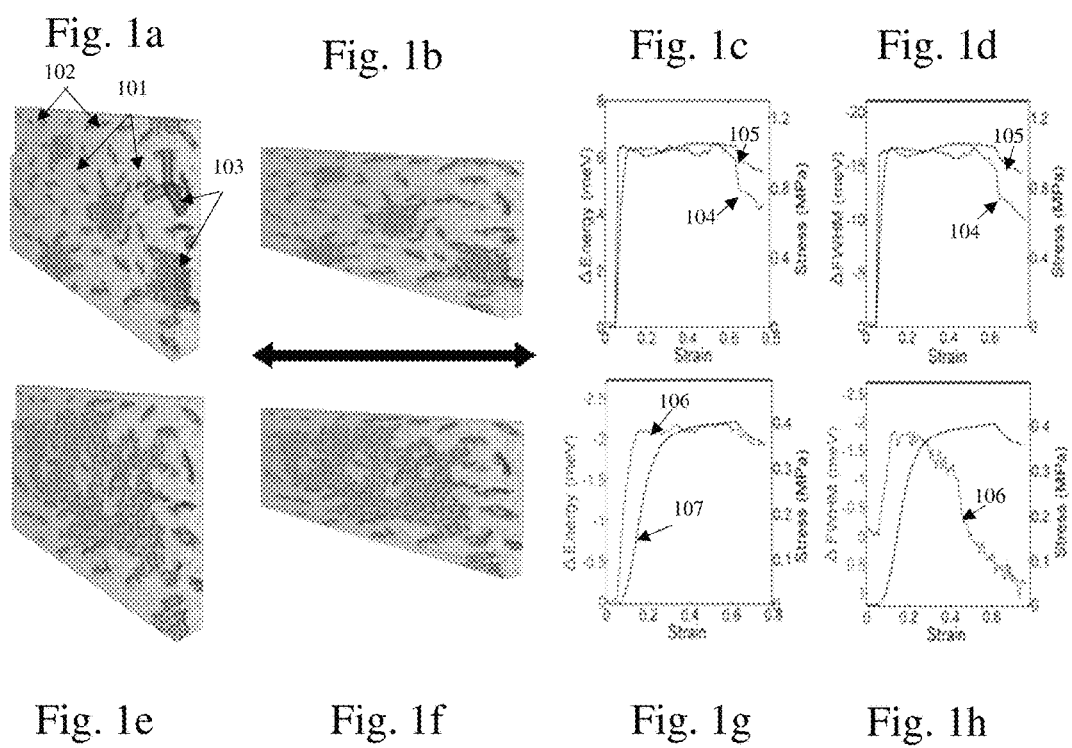

Fig. 3a
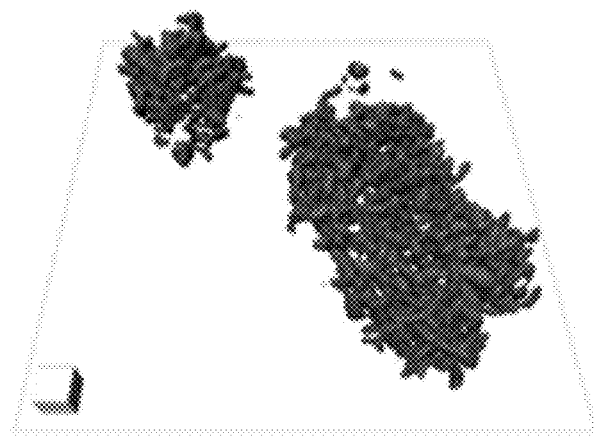
Fig. 3b
Fig. 3c
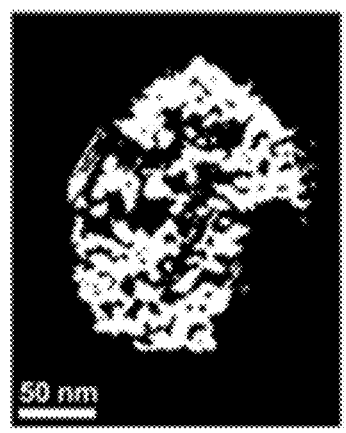
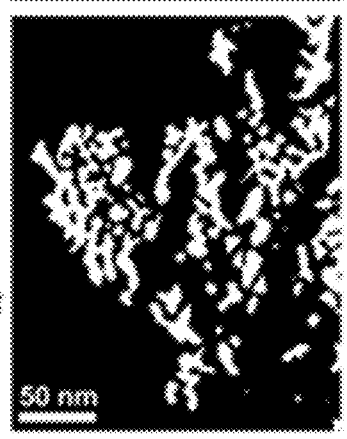
Fig. 3d

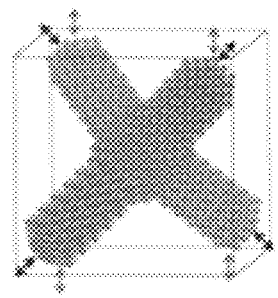
Fig. 4a
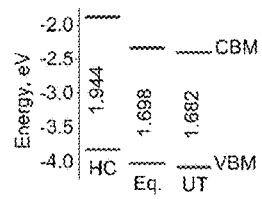
Fig. 4b
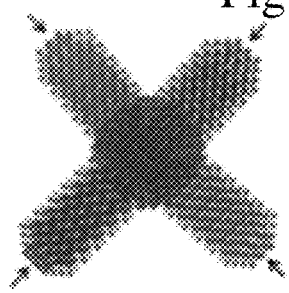
Fig. 4c
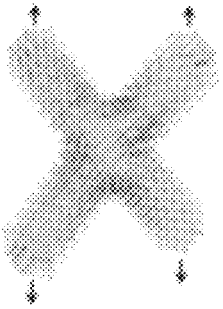
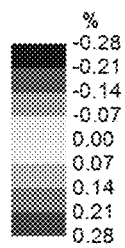
Fig. 4d
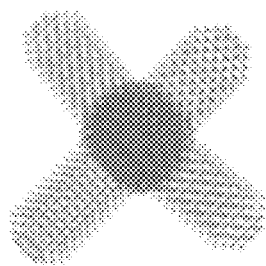
Fig. 4e
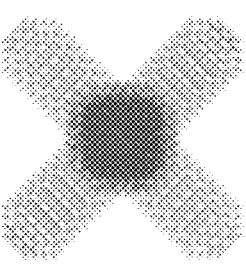
Fig. 4f

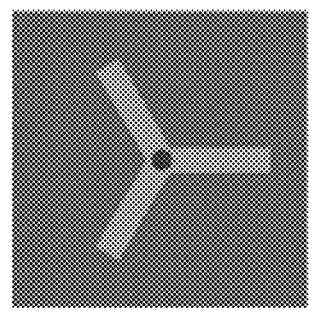
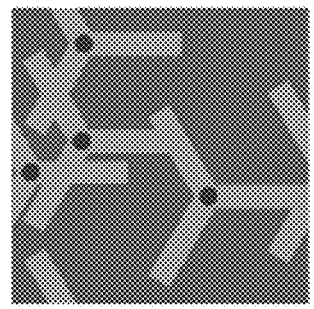
Fig. 5a                Fig. 5b
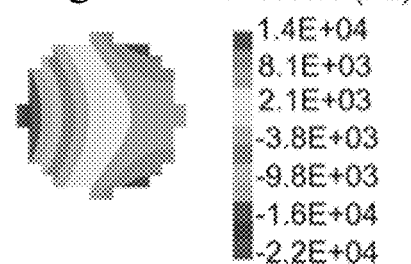
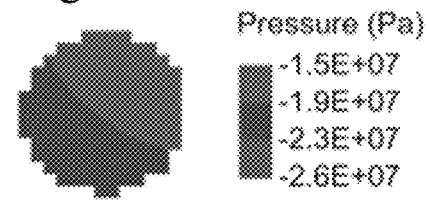
Fig. 5c                Fig. 5d
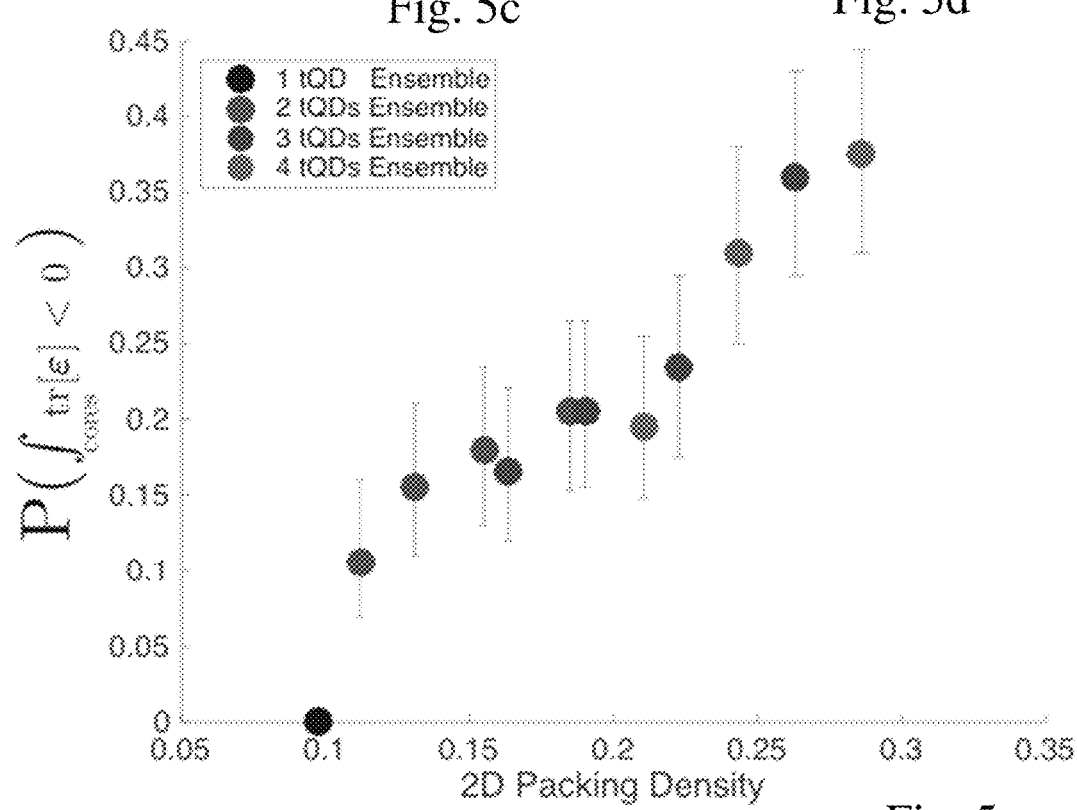
Fig. 5e Fig. 9a
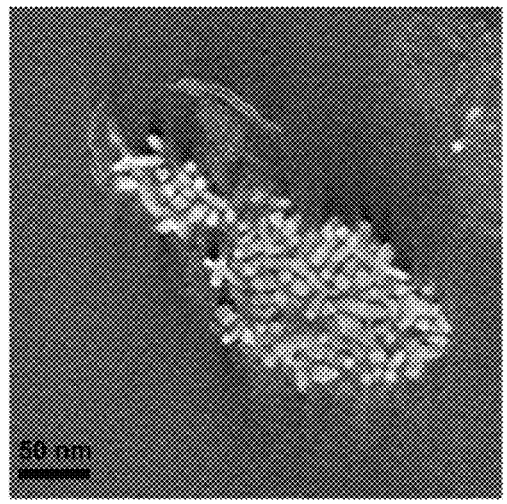
Fig. 9b
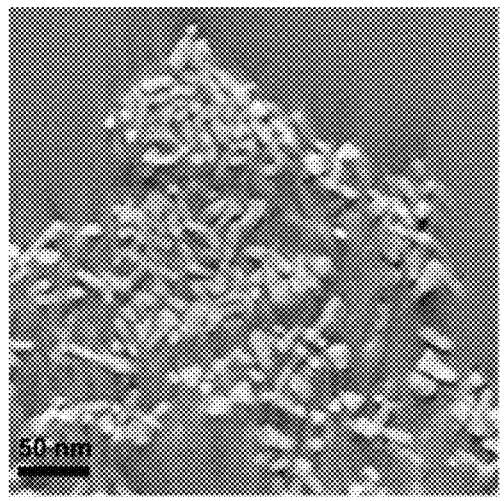
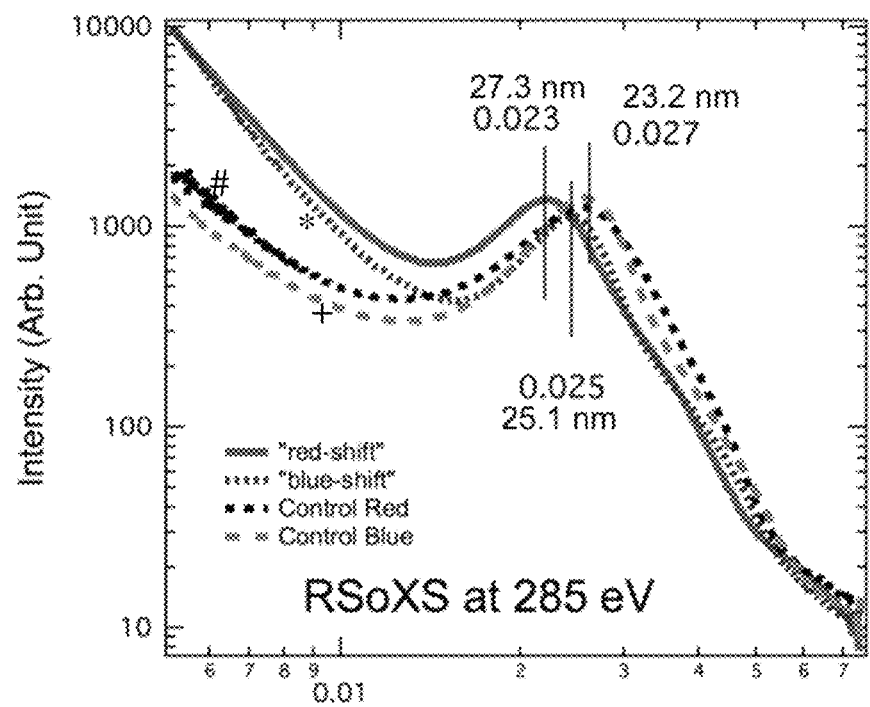
Fig. 9c continues

MECHANISMS OF LOCAL STRESS SENSING IN MULTIFUNCTIONAL POLYMER FILMS USING FLUORESCENT TETRAPOD NANOCRYSTALS

CROSS REFERENCE TO RELATED APPLICATIONS

This application claims priority to U.S. Provisional Application Ser. No. 62/342,653 filed May 27, 2016, which application is incorporated herein by reference as if fully set forth in their entirety.

STATEMENT OF GOVERNMENTAL SUPPORT

The invention described and claimed herein was made in part utilizing funds supplied by the U.S. Department of Energy under Contract No. DE-AC02-05CH11231 between the U.S. Department of Energy and the Regents of the University of California for the management and operation of the Lawrence Berkeley National Laboratory. The government has certain rights in this invention.

BACKGROUND OF THE INVENTION

Field of the Invention

As premature failure of structural components invariably results from the initiation and incipient growth of small cracks, there is a vital need for auto-responsive structural materials that potentially self-detect and self-respond to environmentally-induced mechanical damage. Such materials have a built-in potential to prevent catastrophic failure in service applications.

However, current technologies that can provide for the early self-detection of local stresses associated with incipient cracks are extremely limited. Mechanophoric dyes and piezoresistive materials, for example, are only effective at the millimeter length-scale with relatively low sensitivity; furthermore, such techniques are very challenging to implement "in the field". In addition, many conventional sensing techniques adversely affect the properties of the host material. A visible-light, nanoscale sensor with the ability to be embedded into a variety of "smart" structural materials without causing such degradation would be particularly appealing for the potential sensing of impending fractures in service. Furthermore, mechanical stresses exerted by biological tissues can be signatures of disease. Thus, such a sensor, if embedded into soft polymers, could also potentially be of significant use in biological applications such as sensing of stresses in cancer cell proliferation.

Colloidal semiconductor quantum dots display a multitude of size and shape-dependent properties, enabling their use in a variety of electronic and optical applications. The ability to tune their size and shape, and in particular the ability to create branched nano-heterostructures, provide further opportunities to take advantage of their special behaviors. One such opportunity is the creation of functional nanocomposites with specific "smart" characteristics, such as shape-dependent mechanical properties or self-healing properties upon exposure to radiation.

The cadmium selenide-cadmium sulfide (CdSe—CdS) core/shell tetrapod quantum dot (tQD) is a particularly interesting system. Due to the tQD's bright photoluminescence and branched morphology, in which the four long CdS arms confer a net stress on the CdSe core upon deformation, the tQD exhibits a unique photoluminescence stress response as seen in previous studies in diamond anvil cells, under atomic force microscope (AFM) tips and in semicrystalline polymers. Owing to its nanoscale size and unique shape, the tQD provides a far higher spatial resolution of stresses than existing technologies.

Prior studies on the tQD as a polymer stress sensor have been limited by low sensitivity and the detection of only tensile stresses, and no self-reporting of local composite morphology. Furthermore, sensing was also only demonstrated in polymer fibers, rather than films, and was restricted by an inability to correlate optical and mechanical data as these measurements could not be performed simultaneously.

SUMMARY

One innovative aspect of the subject matter described in this disclosure can be implemented in a stress sensing nanocomposite including a polymer film further comprising a plurality of aggregated fluorescent tetrapod nanocrystals.

In some implementations, the aggregated fluorescent tetrapod nanocrystals comprise aggregated tetrapod quantum dots (tQDs). In some implementations, a volume ratio of tQD/polymer defined by a tQD aggregate fill fraction or a packing density in the aggregated tQDs is approximately between 40%-50%±5% for a compression-sensing nanocomposite and 20%-30%±2% for a tension sensing nanocomposite. In some implementations, a volume ratio of tQD/polymer defined by a tQD aggregate fill fraction or a packing density in the aggregated tQDs is approximately 50%±5% for a compression-sensing nanocomposite and 25%±2% for a tension-sensing nanocomposite.

In some implementations, tQDs are approximately a factor of two farther apart in a tension-sensing aggregate than in a compression-sensing aggregate, and the tension-sensing aggregate has approximately a factor of two times more polymer inside of the tension-sensing aggregate in terms of small-scale inter-tQD regions.

In some implementations, a tensile stress applied to densely-packed tQDs in the polymer results in a blue-shift of a tQD photoluminescence emission maximum due to a uniform compression of tQD cores, and a tensile stress applied to loosely-packed tQDs in the polymer results in a red-shift of a tQD photoluminescence emission maximum due to a net core tension.

In some implementations, the aggregated tQDs for a compression-sensing nanocomposite exhibit a higher energy blue-shift of a tQD photoluminescence emission maximum under tensile stress due to a compression of tQD cores in the aggregated tQDs.

In some implementations, the aggregated tQDs for a tension-sensing nanocomposite exhibit a lower energy red-shift of a tQD photoluminescence emission maximum under tensile stress due to a tension of tQD cores in the aggregated tQDs.

In some implementations, a tQD comprises a cadmium selenide-cadmium sulfide (CdSe—CdS) core/shell tetrapod quantum dot (tQD). In some implementations, a tQD has an arm length of approximately 26±3 nm. In some implementations, a zinc-blende CdSe core has a diameter of approximately 2.8 nm. In some implementations, a wurtzite CdS arm is approximately 4.2 nm in length and 1.9 nm in diameter. In some implementations, the CdSe—CdS core/shell tQD contains approximately 4245 atoms with a chemical formula $Cd_{272}Se_{297}/Cd_{1132}S_{1116}$.

In some implementations, the polymer film comprises a block copolymer. In some implementations, the block copolymer comprises poly(styreneethylene-butylene-styrene) (SEBS). In some implementations, the SEBS comprises approximately 60% polystyrene (PS) and 40% poly(ethylene-butylene) (P-EB).

BRIEF DESCRIPTION OF THE DRAWINGS

FIG. 1 illustrates schematic microstructures and simultaneous mechanical and fluorescence tensile stress-strain curves for compression- and tension-sensing tQD-SEBS polymer nanocomposite films.

FIG. 3 illustrates Electron Tomography Reconstructions of tQD-SEBS Nanocomposites.

FIG. 4 illustrates valence force field simulations and density functional theory of energy levels of stressed tQDs.

FIG. 5 illustrates a finite element analysis of compression-sensing and tension-sensing tQD aggregates in a polymer under tension.

FIG. 9 illustrates slices from electron tomography and soft x-ray scattering of tQD-polymer nanocomposite films.

DETAILED DESCRIPTION

Figures 2A, 2B:
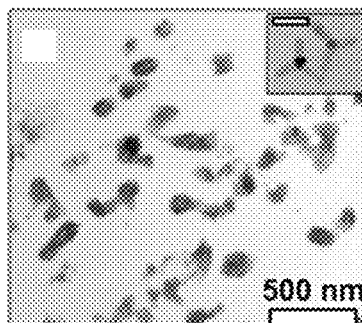
FIG. 2 illustrates TEM and AFM of compression- and tension-sensing tQD-SEBS nanocomposites.
Figures 2C, 2D:
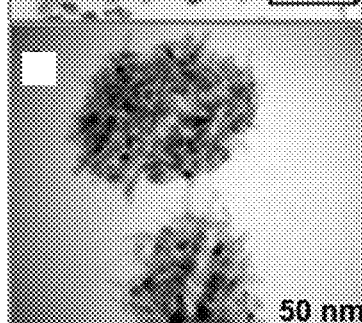
Figures 2E, 2F:
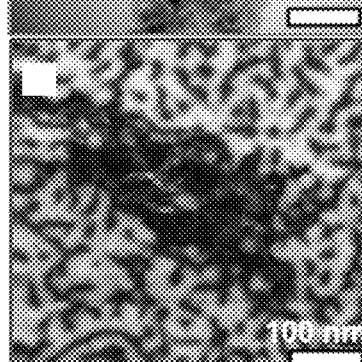
Figure 2G:
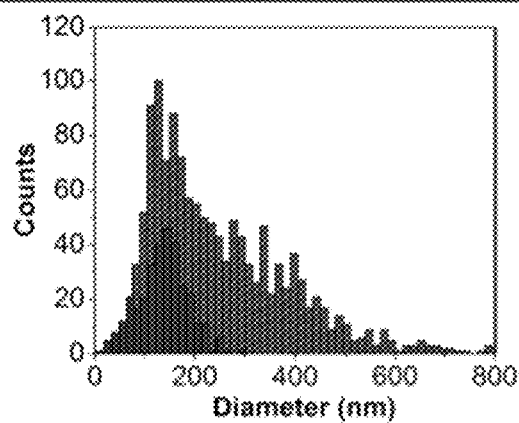

In the discussions that follow, various process steps may or may not be described using certain types of manufacturing equipment, along with certain process parameters. It is to be appreciated that other types of equipment can be used, with different process parameters employed, and that some of the steps may be performed in other manufacturing equipment without departing from the scope of this invention. Furthermore, different process parameters or manufacturing equipment could be substituted for those described herein without departing from the scope of the invention.

These and other details and advantages of the present invention will become more fully apparent from the following description taken in conjunction with the accompanying drawings.

Various embodiments describe a tetrapod quantum dot (tQD) as a detector of nanoscale compressive and tensile stress when embedded into widely-used, low-cost smart structural block copolymer films. Optical sensing during mechanical testing was performed in real time and shows quantitatively the reasonable degree of matching between optical and mechanical curves. For the first time, we describe and illustrate sensing in terms of both photoluminescence emission-maximum and full-width half maximum (FWHM).

In some embodiments, a cadmium selenide-cadmium sulfide (CdSe—CdS) core/shell tetrapod quantum dot (tQD) is described.

The tQD responds to stress via changes of its energy band gap, with the response coming mostly from its CdSe core due to type I band alignment between the core and the CdS arms. Tensile stress decreases the band gap by pulling apart the bonds in the tQD core, while uniform compression increases the band gap by moving the ions in the CdSe core closer together. The photoluminescence emission spectra measured from tQDs embedded in a polymer matrix is then shifted to higher or lower frequency (blue- or red-shift respectively) allowing for a direct measure of local stress.

We show that tensile stress applied to densely-packed tQDs in polymers results in a blue-shift of the tQD photoluminescence emission maximum due to uniform compression of tQD cores, while tensile stress applied to loosely-packed tQDs in polymers results in a red-shift of the tQD photoluminescence emission maximum due to a net core tension. This phenomenon arises from the unique ability of tQDs to self-report subtle changes in nanoscale dispersion and related changes in macroscopic composite mechanical properties, with a switch in optomechanical response from red-shifting to blue-shifting when tQDs are in direct contact. A polymer-embedded sensor that can self-report its own dispersion would be of broad utility for nanocomposite design, and to the best of our knowledge, has never been reported. Due to the unique stress amplification effects of the tQD, the film sensors have two orders of magnitude higher stress response.

Using density functional theory, finite-element modeling, and experimental techniques such as transmission electron microscopy (TEM), electron tomography, characterization of fluorescence as a function of tensile stress, time-resolved photoluminescence spectroscopy, atomic force microscopy (AFM), and soft-x-ray scattering, we reveal the nanoscopic origins of the tQD photoluminescence shifts.

Furthermore, we disclose that tQDs do not degrade the mechanical properties of the polymer films and have unchanged photoluminescence properties even after a year of storage in air; moreover, the film preparation method is scalable to industrial processing. The tQD sensor can be customized to sensing local tension or compression by changes in room-temperature processing. tQDs provide a highly sensitive material to potentially monitor stress distributions around cracks in structural nanocomposites for in service applications, and can potentially be implemented in the field using low-cost, portable equipment.

As previous work has shown the ability of spherical nanoparticles to diffuse to growing cracks in materials and diminish their ability to propagate, the findings of this work could possibly allow for diverse 'smart', dispersion-reporting, self-healing structural tQD-spherical nanoparticle-polymer nanocomposites that can sense local and overall composite mechanics as well as potentially detecting and preventing their own fracture.

The composites in this work were prepared by mixing tQDs in chloroform with the widely used structural block copolymer, poly(styrene-ethylene-butylene-styrene) (SEBS). The SEBS consisted of 60% polystyrene (PS) and 40% poly(ethylene-butylene) (P-EB) with a molecular weight of 117,000 Da. All tQDs were incorporated with their native alkyl chain ligands at a concentration of 20% by weight, or 5% by volume, into SEBS using a solvent-casting method under two separate processing conditions. In other embodiments, ligand exchange may be performed to utilize suitable ligands.

One set of composites was dried under a vigorous nitrogen flow with the drying process completed within 1-2 mins. We refer to these as tension-sensing films due to their decrease (red-shift) in photoluminescence wavelength with applied tensile stress, which as we show below is due to tensile stress in the tQD cores.

The other set of composites were allowed to dry slowly in ambient, with the process completed in 1-2 hrs. We refer to these as compression-sensing films due to their increase in photoluminescence wavelength with applied tensile stress, which as we show below is due to volumetric compressive stress in the tQD cores resulting from direct contact between tQDs.

FIG. 1 illustrates schematic microstructures and simultaneous mechanical and fluorescence tensile stress-strain curves for compression- and tension-sensing tQD-SEBS polymer nanocomposite films. Panels a,b illustrate schematics of the microstructures of tQD-SEBS compression-sensing film (a) before and (b) after application of tensile stress. Light shaded regions 101 represent poly(ethylene-butylene) (P-EB), dark regions 102 represent polystyrene (PS), and tQDs are shown in dense clusters 103. Inset to (a) indicates schematic of a single tQD nanocrystal 103. Panels c,d illustrate the result of simultaneous fluorescence 104 and mechanical test (105 dark black line) for (c) emission maximum shift and (d) FWHM shift for compression-sensing film. Panels e,f illustrate schematics of the microstructures of tQD-SEBS tension-sensing film (e) before and (f) after application of tensile stress. Panels g,h. illustrate the result of simultaneous fluorescence 106 and mechanical test (107 dark black line) for (g) emission maximum shift and (h) FWHM shift for tension-sensing film. Black double arrow indicates direction of applied tensile stress.

FIG. 1 shows schematic illustrations of the compression-sensing and tension-sensing films prepared via the two above mentioned protocols, before and after application of tensile stress. Likely due to the imperfect interface between the tQDs and SEBS, tQDs partially phase separate, forming small dense assemblies in the compression-sensing films and sparse, larger ones in the tension-sensing films. In both cases, tQD assemblies are uniformly distributed throughout the polymer films.

The fluorescence properties of both films were studied under tensile deformation using an inverted fluorescence microscope (see FIG. 1). Understanding of the tQD stress response requires knowledge of an agreement between optical and mechanical tests. Here we examine the concept of tQD mechano-optical sensing by coordinating mechanical and optical data acquired simultaneously. Our composites were deformed uniaxially to a maximum strain of 60% and held to evaluate stress-relaxation behavior.

Figure 6A:
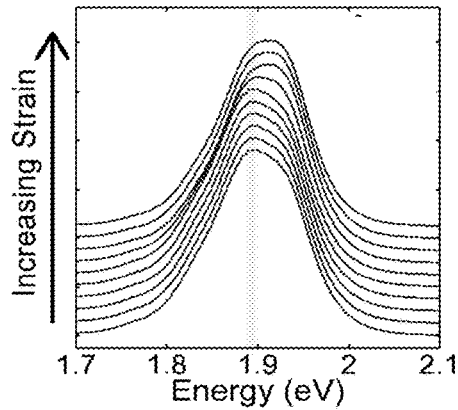
FIG. 6 illustrates raw photoluminescence spectra and fitted average emission maximum shifts of tetrapod quantum dot (tQD)-polymer nanocomposites.
Figure 6B:
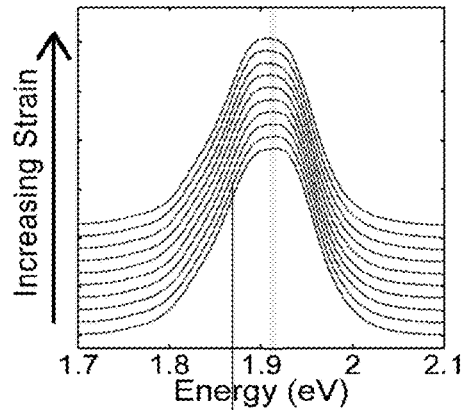
Figure 6C:
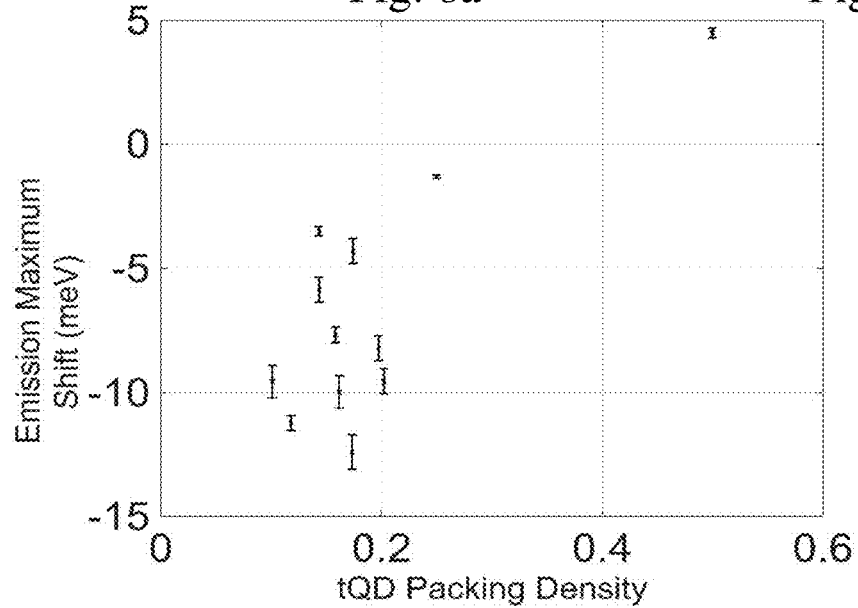

The mechano-optical sensing behavior, depicted in FIG. 1, shows a fluorescence shift of the tQD-SEBS composites in the compression-sensing and tension-sensing films as a function of applied strain, along with the corresponding mechanical loading curves (105,107 dark black lines) (see also FIG. 6). The results of peak position and FWHM for compression-sensing nanocomposites (panels c-d) indicate excellent agreement between the mechanical loading curve and the optical sensing curve. Most of the emission maximum shift occurs in the elastic region, in which a slope of 8.6±0.9 meV/MPa is measured as well as a maximum optical shift of 4.5±0.4 meV. The fluorescence curve additionally shows variation in the nonlinear region, and matches the exponential behavior of the mechanical stress relaxation well.

We also see fairly good opto-mechanical agreement in the tension-sensing composites (see panel (f) of FIG. 1), although not as good as in the compression-sensing composites (see panel (b) of FIG. 1). The maximum fluorescence red-shift occurred mainly in the elastic region, which had a slope of −2.4±0.3 meV/mPa and a maximum optical shift of 1.3±0.14 meV.

We find that for compression-sensing films, the FWHM of the spectra follows the stress-strain curve of the composite (see panel (f) of FIG. 1). Additionally, the FWHM sensitivity in stress and strain, −39±5 meV/MPa and −300±30 meV/strain, respectively, is significantly higher than previously reported tQD emission maximum response sensitivity. This additional sensing mode is not observed in any of the tension-sensing films (see panel (g) of FIG. 1) or in any previous studies in tQD fiber composites. Unlike in the compression-sensing films, and as in previous work, the photoluminescence FWHMs in tension-sensing films exhibit a slight increase (g) but do not track the stress-strain curve.

All sensitivities, or pressure coefficients, reported in units of shift/stress (meV/MPa) show significant improvements over the values reported for bulk CdSe. This is perhaps due to the unique geometry of the tQDs, in which the CdS arms act as antennas that amplify and transfer stress from the environment to the CdSe core. Indeed, this was also seen in our finite-element simulations, as discussed below. Our tQD films sense stress with an optical deformation response three orders of magnitude more sensitive than previous tQD sensors, making them equal or better in sensitivity than several other key local stress-sensing technologies (see Supplementary Note 1).

Figure 7A:
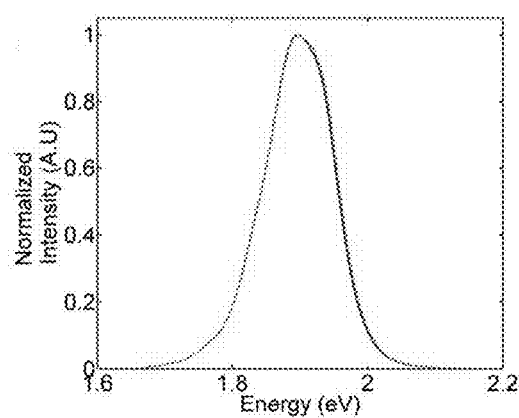
FIG. 7A illustrates raw photo-luminescence spectra of compression-sensing and tension-sensing tQD-polymer nanocomposites before and after prolonged storage in ambient conditions.
Figure 7B:
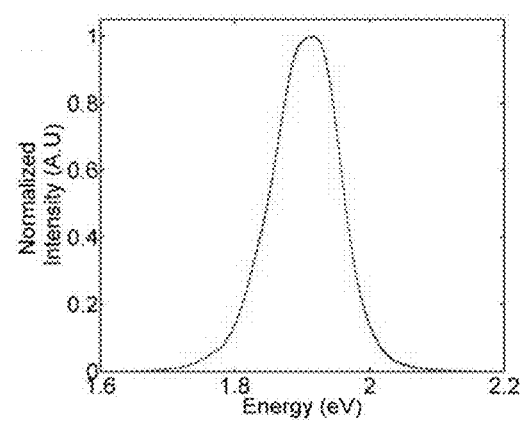
FIG. 7B illustrates raw photo-luminescence spectra of compression-sensing and tension-sensing tQD-polymer nanocomposites before and after prolonged storage in ambient conditions.

The films exhibited nearly identical optical and mechanical properties even after a year of storage in air (see FIGS. 7A and 7B). The sensing is very repeatable; 20+ cycles of stretching to ~60% strain performed on the same sample led to nearly identical sensor responses with a return to the same baseline fluorescence FWHM and emission maximum in-between tests. This likely indicates that the tQDs are experiencing fully elastic deformation during the stress-sensing in the polymer. Compared to control samples, the ductility and toughness of the compression-sensing and tension-sensing films were unchanged.

We investigated the possibility that the blue-shift under tension could be due to better Forster resonance energy transfer (FRET) efficiencies in close-packed aggregates. However, this is unlikely as we found no difference in photoluminescence rise time or initial lifetime decays between compression- and tension-sensing films (see FIGS. 8A and 8B).

The different, opposite, photoluminescence shifts in tension-sensing and compression-sensing composites are rather striking since the films only differ in their drying time. To investigate whether the microscopic structural differences between these two films were responsible for their disparate sensing behavior, transmission electron microscopy was used to determine their microstructures.

FIG. 2 illustrates TEM and AFM of compression- and tension-sensing tQD-SEBS nanocomposites. Panels a-b illustrate low magnification TEM micrographs of (a) compression-sensing and (b) tension-sensing films. Inset to (a) indicates tQDs before polymer encapsulation. Inset scale bar is 40 nm. Panel c illustrates higher resolution TEM images of compression-sensing and panel d illustrates tension-sensing films showing that they are composed of tQDs.

Panels e-f illustrate AFM micrographs of panel e compression-sensing and panel f tension-sensing films. Panel g illustrates size distributions of diameters of tQD aggregates in compression-sensing and tension-sensing films. Darker and lighter histograms represent size distributions for compression-sensing and tension-sensing films respectively.

The images shown in FIG. 2 show that the two films exhibit very different morphologies. Qualitatively, the compression-sensing tQD contains densely-packed aggregates which appear darker than the tension-sensing aggregates in the TEM images. The tension-sensing aggregates are less dense and have a large number of 10-500 nm diameter inter-tQD regions, as seen in panels b,d. Due to the fast diffusion constant of the polymer chains in solution during drying ($>10^{17}$ $cm^2/sec^{38}$) and the rate of the drying processes employed, these regions are likely filled with polymer.

This was confirmed by electron tomography (see FIG. 3) which shows that the inter-tQD regions are filled with matter consistent in contrast with the polymer material outside the aggregates. Panel (g) of FIG. 2 shows histograms of aggregate diameters for compression-sensing and tension-sensing aggregates, respectively, from several TEM images. In general, tension-sensing aggregates have a diameter some two times greater than compression-sensing aggregates. Panel (g) of FIG. 2 also shows that the quickly-dried tension-sensing material contains some large aggregates as indicated by the asymmetric histogram with a large tail, while the slowly-dried compression-sensing aggregates have a more symmetric size distribution. The change in packing density that results in a switch from red- to blue-shifting, or tension- to compression-sensing, is accompanied by a Young's modulus increase of a factor of two. Thus, tQDs do not only report subtle changes in the nanoscale dispersion of the composite filler phase, but also can serve as a visible-light indicator of associated changes in mechanical properties.

To investigate whether the polymer morphology and microdomain organization may have been altered by the different drying conditions, we acquired AFM phase images of the compression-sensing and tension-sensing aggregates. The AFM images are shown in panel (e-f) of FIG. 2 with the same resolution and field of view. An entire compression-sensing aggregate is imaged in panel (e) of FIG. 2, but only part of a tension-sensing aggregate can be seen in panel (f) of FIG. 2. In the region around the aggregates, light shade represents polystyrene, and dark shade represents P-EB, as described in more detail in the Methods section. The AFM results indicate a morphology with cylindrical and lamellar P-EB regions in a PS matrix, and show little to no difference in the microdomain spacing and distribution of polymer around the aggregates in the tension-sensing and compression-sensing films, which was confirmed by ruthenium tetroxide staining.

Traditional TEM projection images are sufficient to determine the large-scale ($>100$ nm) porosity inside the aggregates, but the overlap of many tQDs in projection obscures their 3D distribution and the small-scale ($<10$ nm) inter-tQD regions. We utilized STEM electron tomography to determine the internal distribution of the tQDs and polymer inside of the aggregates.

FIG. 3 illustrates Electron Tomography Reconstructions of tQD-SEBS Nanocomposites. Panels (a) and (b) illustrate perspective images of isosurface reconstruction of tension-sensing and compression-sensing aggregates produced by electron tomography. The inset white scale cube has 25 nm sides. Panels (c) and (d) illustrate thresholded 1.13-nm slices of the tomogram representative of the internal structure of the compression-sensing and tension-sensing aggregates, respectively.

Panels (a-b) of FIG. 3 show images of isosurface renderings of 3D electron tomography reconstructions for both the compression-sensing and tension-sensing composites. The tomography was performed using cryo-microtomed cross-sections with a thickness (~70-90 nm) smaller than the diameter of the aggregates (~150 nm). The tomographic images revealed small regions of polymer ~10 nm in diameter which were inside the aggregates and not visible in the TEM projection images (see panels (c-d) of FIG. 2).

The analysis of small-scale porosity from each individual slice of the tomography reconstructions showed that the volume ratios of tQD/polymer (which we term tQD aggregate fill fraction, or packing density) in the aggregates were 50%±5% and 25%±2% for compression-sensing and tension-sensing aggregates, respectively. This small-scale porosity can be viewed as an approximation of the distance between adjacent tQDs, as tQDs have arm lengths of 26±3 nm.

These results illustrate that individual tQDs are about a factor of two farther apart in the tension-sensing aggregates than in compression-sensing aggregates, and that the tension-sensing aggregates have a factor of two times more polymer inside of them in terms of small-scale inter-tQD regions. They also indicate that, in the aggregates, the tQDs are in direct contact, separated only by their thin outer ligand coating (see FIG. 9). Results on resonant soft x-ray scattering of the respective samples are given in Supplementary Note 2 and FIG. 9. Only red-shifts were seen at a variety of tQD packing densities below 50%, including homopolymers and cases in which tQDs are singly dispersed (see FIG. 6). Due to the colloidal nature of tQDs, and their smart ability to self-report whether they are in direct contact, they potentially could enable auto-responsive, multifunctional structural nanocomposites that would self-predict local and bulk mechanical properties as well as impending fracture.

Having shown how the aggregates differ structurally, we now use electronic structure calculations to illustrate the underlying mechanism of photoluminescence shifts due to an applied mechanical stress. We performed atomistic density functional theory simulations on tQDs with zinc-blende CdSe cores of 2.8 nm, wurtzite CdS arms of 4.2 nm in length and 1.9 nm in diameter; containing 4245 atoms with chemical formula $Cd_{272}Se_{297}/Cd_{1132}S_{1116}$, with pseudo-hydrogen passivation.

This is described in more detail in Supplementary Note 3 and FIG. 10. We found that both the conduction band minimum state and valence band maximum state are located in the CdSe core, in agreement with experiments. To simulate stressed tQDs, an atomistic valence force field model was used to calculate the atomic positions under different stresses. The different stress states include uniform bond distance scaling (isotropic compression and tension) and uniaxial pushing or pulling at the tips of the four arms (uniaxial compression and tension) (see FIG. 4) (see Supplementary Note 3 for details on stress states, such as torsion).

FIG. 4 illustrates valence force field simulations and density functional theory of energy levels of stressed tQDs. Panel a illustrates an atomic structure of and schematic of stress application to modeled CdSe/CdS core-arm tQD: zinc-blende CdSe core. Panel b illustrates energy level changes of stressed tQDs. HC represents energy level changes for a tQD under hydrostatic compression, Eq. represents the energy levels for a tQD at equilibrium (no stress), and UT represents the energy levels for a tQD under uniaxial tension. Panels c-d illustrate distribution of stresses in tQDs that are (c) compressed isotropically and (d) stretched uniaxially. Colorbar shows percent change in volume. Panels e-f illustrate equilibrium (unstressed) wave function charge densities of the valence band maximum and conduction band maximum, respectively.

Only the uniform, volumetric compression case results in a blue-shift. Among the red-shift cases, the situation most relevant to the experiment is uniaxial tension. The local strain of the tQD under uniaxial tension is shown in panel (f) of FIG. 4. Near the CdSe core, there are both positively and negatively dilated regions. This makes the red-shift relatively small. Considering that 2.5% strain was applied, which is likely much higher than the experimental tQD strains due to imperfect stress transfer to the tQD, the theoretically obtained band gap changes were much higher than the experimentally observed shifts. Table 1 shows the changes in the valence band minimum and conduction band maximum under the different tQD deformations. In summary, the theoretical results revealed that only deformations that caused a net decrease in volume of the CdSe core produced a blue-shift of the energy levels.

TABLE 1

Calculated energy levels of the tQD under different deformations (all deformations consist of a 2.5% change in linear dimensions).

| | VBM, eV | CBM, eV | Band gap (Eg), eV | ΔEg, meV |
|---|---|---|---|---|
| equilibrium | −4.022 | −2.324 | 1.698 | — |
| uniaxial tension | −4.072 | −2.390 | 1.682 | −16 |
| uniaxial compression | −3.934 | −2.253 | 1.681 | −17 |
| isotropic tension | −4.179 | −2.753 | 1.435 | −263 |
| hydrostatic compression | −3.818 | −1.874 | 1.944 | +246 |

To investigate how tQD core compression may arise under overall uniaxial tension of the polymer nanocomposite, we conducted voxel-based micromechanical finite-element analysis simulations of tQDs in a polymer matrix using the Finite Element Analysis Program (FEAP). The simulations used periodic boundary conditions and net average uniaxial loads for a range of packing densities utilizing multiple random configurations to generate valid statistics. As the focus of the analysis was an elucidation of the mechanism leading to net compression of the core, two-dimensional simulations were performed to ease the cost and complexity. Previous comprehensive work considering comparing some nine 2D and 3D unit cells showed only a 5-10% difference in the results for elastic modulus; since the majority of the blue-shifts and red-shifts that are observed occur in the elastic region, this is further justification for use of a 2D finite element model.

FIG. 5 illustrates a finite element analysis of compression-sensing and tension-sensing tQD aggregates in a polymer under tension. Panels (a) and (b) of FIG. 5 finite element analysis images of low density (tension-sensing) and high density (compression-sensing) tQD aggregate unit cells. In the configurations shown, compression-sensing aggregates have 28% tQDs by area and an applied uniaxial stress of 0.53e+4 Pa, while simulated tension-sensing aggregates have 9.6% tQDs by area and an applied uniaxial stress of 0.14e+4 Pa. Panel (c) is a pressure map of a tension-sensing tQD core from panel (a). Panel (d) is a pressure map of a compression-sensing tQD core from panel (b). Panel (e) illustrates the probability that a given tQD configuration at a given tQD volume fraction, or packing density, in an aggregate will result in a net average volumetric compression in the tQD cores. Black 1, red 2, blue 3, and magenta 4 respectively represent ensembles with one, two, three, and four tQDs.

Two example configurations are illustrated for low (see panel (a) of FIG. 5) and high (see panel (b) of FIG. 5) tQD aggregate volume fractions, or packing densities. Panel (c) of FIG. 5 shows the typical pressure response of a CdSe core in the low packing regime; the integral of the pressure field is positive, indicating the overall response is tensile. In contrast see panel (d) of FIG. 5 shows a typical pressure response in a CdSe core in the high packing regime; the integral of the pressure field is negative indicating the overall response is compressive. Though it varied significantly depending on the tQD location in the aggregate, the average core stress across all cores and configurations was of similar magnitude for net compressive and net tensile cases.

The mechanism leading to the compressive case is one in which the CdS arms strongly interact due to close proximity and have a large span in the direction orthogonal to the loading, i.e., tQDs serve as sensors of nanoscale dispersion, with a dichotomy in response characteristic (e.g., red-shift or blue-shift, or compressive or tensile) depending on whether or not adjacent tQDs are interacting.

By simulating a large ensemble of configurations (~200) we gain a statistical estimate of the probability that a given packing density will lead to a situation in which uniaxial tension gives rise to a net volumetric compression of the CdSe cores in an aggregate (see Supplementary Note 4 for details). As shown in panel (e) of FIG. 5, high packing densities lead in a near linear fashion to higher probabilities of net compressive cores over the range of packing densities from ~10 to ~30% (the upper limit of what can be sensibly simulated in two dimensions).

The finite-element analysis reveals a substantial core stress amplification of up to a few orders of magnitude in the tQD for both volumetric compression and tensile stress cases, qualitatively consistent with experimental observations.

FIG. 6 illustrates raw photoluminescence spectra and fitted average emission maximum shifts of tetrapod quantum dot (tQD)-polymer nanocomposites. Panels (a-b) illustrate raw photo-luminescence spectra of (a) compression-sensing and (b) tension-sensing films as a function of applied tensile stress ranging from 0-15% strain. Black lines are eye guides. Panel (c) illustrates emission maximum shift as a function of tQD packing density for twelve tQD-polymer nanocomposites.

FIGS. 7A and 7B illustrate raw photo-luminescence spectra of compression-sensing and tension-sensing tQD-polymer nanocomposites before and after prolonged storage in ambient conditions. FIG. 7A illustrates Photo-luminescence spectra of compression-sensing films before (black) and after (magenta) prolonged storage in ambient. FIG. 7B illustrates Photo-luminescence spectra of tension-sensing films before (black) and after (magenta) prolonged storage in ambient.

Figure 8A:
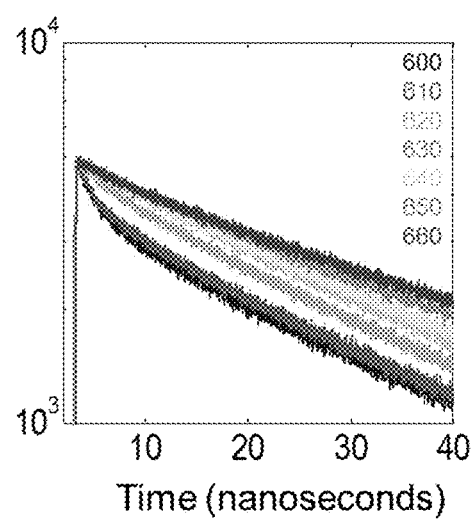
FIG. 8A illustrates time-resolved photoluminescence decays of tQD-polymer nanocomposite films excited at 407.1 nm with a frequency of 1 megahertz.
Figure 8B:
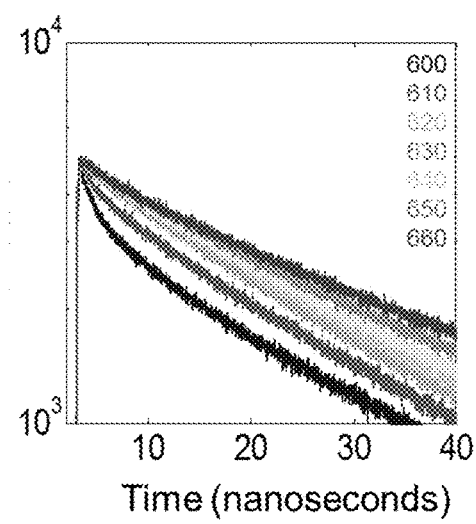
FIG. 8B illustrates time-resolved photoluminescence decays of tQD-polymer nanocomposite films excited at 407.1 nm with a frequency of 1 megahertz.
Figure 10A:
FIG. 10 illustrates tQD Frontier orbital charge distributions from atomistic ab initio density functional theory computations.
Figure 10B:
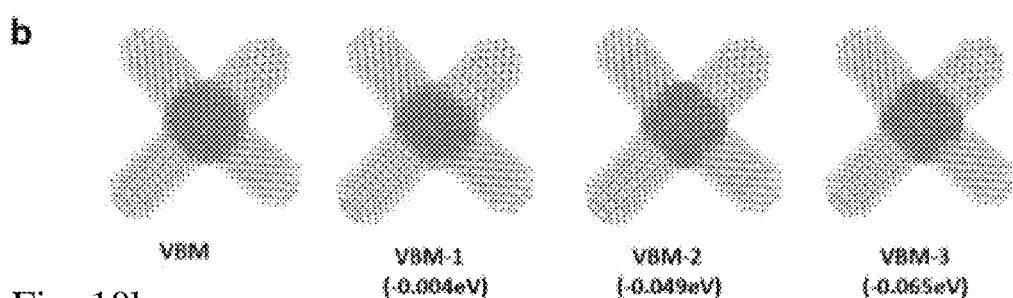
Figure 10C:
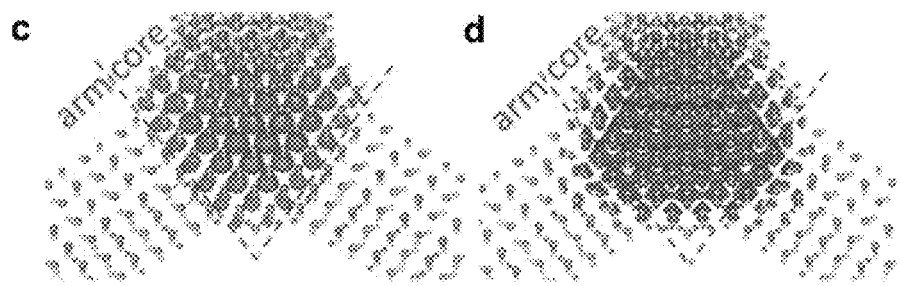
Figure 10D:
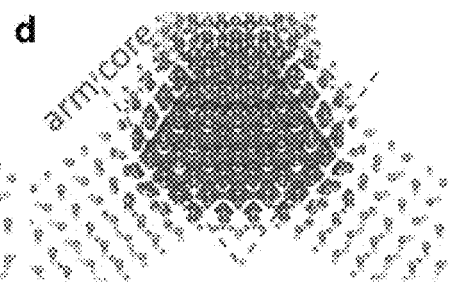

FIGS. 8A and 8B illustrate time-resolved photoluminescence decays of tQD-polymer nanocomposite films excited at 407.1 nm with a frequency of 1 megahertz. FIG. 8A illustrates time-resolved photoluminescence decays for compression-sensing films presented at seven collection wavelengths ranging from 600-660 nm. FIG. 8B illustrates tTime-resolved photoluminescence decays for tension-sensing films.

FIG. 9 illustrates slices from electron tomography and soft x-ray scattering of tQD-polymer nanocomposite films.

Panels (a-b) illustrate two slices 1.38 nm in thickness from the 3D reconstruction of the (a) tension-sensing material and (b) compression-sensing material. The CdSe/CdS tQDs are shown as white contrast and the surrounding polymer is shown as gray background. Of note are the small 2-3 nm spaces between the tQDs indicating that they are in direct contact and separated only by their thin outer ligand coating. Panel (c) illustrates resonant soft x-ray scattering (284.8 eV) spectra of tension-sensing (red-shifting) and compression-sensing (blue-shifting) tQD samples (red-(solid) and blue (*) curves, respectively) and quickly dried and slowly dried SEBS without tQDs (control samples) (green (+) and black curves (#), respectively). The primary scattering peak is observed at ~0.023 $A^{-1}$ for the tension-sensing sample and ~0.025 $A^{-1}$ for the compression-sensing sample, and ~0.027 $A^{-1}$ for both of the control samples. Q-vectors and corresponding real space values are indicated on the figure.

FIG. 10 illustrates tQD Frontier orbital charge distributions from atomistic ab initio density functional theory computations. Panel (a) illustrates charge distributions of the conduction band minimum (CBM) and higher energy levels. Panel (b) illustrates charge distributions of the valence band maximum (VBM) and lower energy levels. In parentheses are values of higher (+1, +2, etc.) or lower (−1, −2, etc.) energy levels relative to the corresponding CBM or VBM. Panels (c,d) illustrate wave function charge densities of VBM (a) and CBM (b) show better confinement of the VBM wave function to the CdSe core, while the CBM wave function penetrates slightly into the CdS arms.

In summary, we have presented here a tQD/polymer nanocomposite system produced by low-cost, scalable colloidal processing which can act as a local sensor of tensile or compressive stresses. The stress is measured as shifts in the emission maximum and the full-width half maximum of the photoluminesence spectra, and is readily measurable in structural parts in service using commonly available portable spectrometers and light sources (see Supplementary Note 5).

We show the unique capacity of tQDs to respond to subtle changes in their own nanoscale dispersion and mechanical properties, with a switch in optomechanical response when tQDs are in direct contact. The sensitivity of the responses to deformation is three orders of magnitude greater than for current state-of-the-art tQD sensors and approaches or exceeds existing technologies.

Moreover, the inclusion of tQDs in the polymer does not degrade the mechanical properties of the polymer matrix, and there is no reduction in response over >20 cycles of deformation. Simulations show that blue-shifts and red-shifts are due to compression and tension of the tQD core, respectively, during tensile deformation of the entire nanocomposite.

The solution-processed tQD merges colloidal synthesis, interfacial tunability, and high sensitivity due to its geometry-borne stress-amplification. The tQD enables facile, scalable introduction into composite materials combined with effective local and bulk sensing capabilities. The tQD's ability to self-detect its own nanoscale dispersion in a composite results in a unique optical nanosensor that can self-report local as well as macroscopic composite properties, a potentially important characteristic for the design of "smart" polymer nanocomposites. Based on the previously established ability of spherical nanoparticles to diffuse to cracks in polymers and diminish their ability to propagate[4], the results in this work could also engender tQD-spherical nanoparticle nanocomposites that could serve as multifunctional, auto-responsive, self-healing, structural parts potentially capable of predicting their own failure in service.

Methods

CdSe—CdS tQDs were prepared as before. The tQDs had arm length 26±3 nm and diameter 6±0.8 nm. SEBS was provided by Kraton (MD 1537) and dissolved in chloroform (Sigma Aldrich) to create solutions of 150 mg SEBS/~10 mL chloroform for compression-sensing films and 25 mg SEBS/~2 mL chloroform for tension-sensing films. tQDs coated with native hydrophobic ligands were dissolved in chloroform and added to the polymer solutions at concentrations of 20% by weight/5% by volume of polymer. These precursor solutions were cast into glass petri dishes for compression-sensing films, and allowed to dry under ambient conditions followed by placing under vacuum. The drying process took 5-8 hours. For tension-sensing films, precursor solution was added to a glass vial and subjected to a highly vigorous flow of nitrogen gas resulting in film drying occurring within 1-2 minutes.

The ~75-100 μm thick films were cut into strips 3-20 mm long×1-3 mm wide for tensile tests, and were clamped using flat grips into a tensile rig employing a Mark-10 0.5 N load-cell. A screw-driven stage connected to a controller (OptoMike OMEC-2BF) was used at a strain rate of $5 \times 10^{-03}$ $sec^{-1}$. 19 trials were performed for compression-sensing films, and 13 trials for tension-sensing films. Tests were performed by stretching the sample to a strain of ~0.6 and holding for 28.5 seconds for stress relaxation. To assess repeatability, the same film was cycled >20 times.

To monitor fluorescence while stretching, the rig had a hole for laser passage, and was mounted onto a metal plate for stability. We used an inverted fluorescence microscope with a spectrometer (Acton, SpectraPro-3001) and CCD (Princeton, 7509-0001). Exposure times of 1 s were used to collect spectra with 0.6 s between frames. We used 488-nm Ar+ laser excitation (Lexel Laser, Inc., 95) with 1-W power and 150-μm spot size. We excited/measured photoluminescence from the core due to the type I band alignment, which localizes the electron and hole to the core, and to our 488 nm excitation. Spectra were collected over the laser spot and fit to single Gaussians. Change in emission was defined as the difference between the peak position at time t and at zero strain.

For TEM, sections ~70-90 nm were cut from ~100 um thick films using an RMC MT-X Ultramicrotome (Boeckler) at cryogenic temperature and picked up from water onto copper grids. Staining was performed using $RuO_4$ to darken PS regions. Stained sections were imaged using a 200 kV Tecnai G220 S-TWIN. Unstained sections were imaged using a 200 kV Tecnai G2. AFM samples were prepared similarly, and were not stained. AFM images were obtained with a scanning probe microscope "NEXT" (NT-MDT) in amplitude modulation mode with a Si probe (spring constant 3.5 N/m). Height and phase images were recorded at the low force level ($A_{sp}$=10 nm, $A_0$=12 nm) and high force ($A_{sp}$=10 nm, $A_0$=24 nm) level. $A_{sp}$ is set-point amplitude, while $A_0$ is free oscillation of the probe prior to sample interaction. Contrast in the phase images at low force varies from ~0-10 degrees and in phase images recorded at high force, ~0-80 degrees. We performed quantitative mapping of elastic modulus in Hybrid mode (a non-resonant oscillation mode in which the sample is modulated at 1.5 kHz). This allowed assigning of light-colored phase blocks to PS and darker blocks to softer PEB.

Tomography was performed using an FEI Titan 80-300 TEM operated in high-angle annular dark field STEM mode at 200 kV with a 10-mrad convergence angle. A tilt-series was acquired with 1.5° steps from ±70°, reconstructed using the IMOD software package. To calculate tQD/polymer packing density, the 3D density was filtered with a 3×3×3 3D median filter and thresholded to distinguish tQD from polymer. The polymer/tQD volume ratio was calculated using all voxels within a boundary defined by a convex hull calculation. For average aggregate size and size distribution, a custom image segmentation Matlab algorithm was developed to outline aggregates. >200 aggregates were used to for histograms. The diameter was computed from a circle with the same area as the aggregate. Compression-sensing aggregates had a diameter of 134±5 nm, while tension-sensing aggregates had a diameter of 292±9 nm. For finding tQD/polymer packing density from TEM images, we estimated the aggregate volume fraction of the polymer from the 2D aggregate fill factor and divided the nanoparticle volume fill fraction by this quantity.

Time-resolved photoluminescence lifetime measurements on compression-sensing and tension-sensing films were performed with a Picoquant FluoTime 300 employing a PMA 175 detector. An LDH-P-C-405 diode laser (excitation wavelength 407.1 nm) was used with a repetition rate of 1 MHz. Reported errors are standard error of the mean, except for nanoparticle sizes, which are mean and standard deviation.

Supplementary Note 1: Stress Sensing Sensitivity of Tetrapod Quantum Dot (tQD)-Polymer Nancomposite Films.

The sensitivity of a probe can be defined by $S=(R/R_O)P$, a common index of quantification for most sensing technologies, where R is the change in sensor response, $R_O$ is the baseline response, and P is the phenomenon under study, in this case, stress. In this work, we now see much improved sensitivity, making the tQD comparable or superior in sensitivity to other key local stress-sensing technologies reported to date. The compression-sensing tQD-film nanocomposites have a stress sensitivity of 4.5e-6 $kPa^{-1}$, which is three orders of magnitude higher than previous tQD sensors and similar to or higher than common mechanochromic dyes, gold nanoparticle chain plasmonic sensors, and stress-sensitive metal nanoparticles, which have sensitivities of 1.9e-5, 4.1e-10, and 2.2e-6 $kPa^{-1}$, respectively. The tQD is thus a complementary method to these existing techniques, with the added advantage of full cyclability, adaptability to almost any polymeric matrix because of its colloidally stable, readily tunable ligand coating, and lack of degradation to the mechanical properties of the host material.

Supplementary Note 2: Resonant Soft X-Ray Scattering Characterization of tQD-Polymer Nanocomposite Films.

Small angle x-ray scattering (SAXS) experiments were carried out to provide statistical information as support to TEM and AFM results. Conventional SAXS relies on the electron density contrast between materials. Since the tQD has much higher electron density compared to the polymers, the SAXS signal was dominated by the tQD aggregates and it was not possible to observe the polymer phase separation. Therefore, resonant soft x-ray scattering (RSoXS) was used to characterize block copolymer morphology in compression-sensing and tension-sensing films. The RSoXS experiment was carried out at BL11.0.1.2 at the Advanced Light Source, Lawrence Berkeley National Lab. Using x-rays with photon energies close to the absorption edges of the constituent atoms in the material, RSoXS combines conventional x-ray scattering with the chemical sensitivity provided by soft x-ray spectroscopy. By turning the x-ray energy, the contrast between materials as well as sensitivity to a specific phase in the complex system can be adjusted. Thin film samples were obtained by cryo-microtomy, and cryo-microtomed films were supported by silicon nitride membranes (Norcada). The sizes of the samples were ~100 μm by 300 μm with thickness ~70-90 nm. RSoXS was measured in transmission geometry and the data was collected with an in vacuo CCD camera (Princeton Instruments) at a series of photon energies near the carbon edge. Strong scattering peaks was observed at ~285 eV, which is the resonant energy for the polymers where the contrast between two polymer blocks was enhanced. For the control samples (polymers dried at the two drying speeds described in the main text without tQDs), the scattering features corresponding to the block copolymer phase separation were observed at all energies. However, for the samples containing tQDs, the block copolymer peaks were only observed at the resonant energies.

FIG. 8 shows the radially-averaged RSoXS results for the tension-sensing (quickly-dried) and compression-sensing (slowly-dried) and control samples.

For the tension-sensing sample, the primary scattering peak is observed at 0.023 $Å^{-1}$, which corresponds to a real space size of ~27 nm. This size is corresponding to the block copolymer phase separation. For the tension-sensing sample, the primary peak is observed at ~0.025 $Å^{-1}$, which corresponding to a 25 nm spacing. For the control samples with both fast- and slow-drying condition, the primary scattering peaks were at ~0.027 $Å^{-1}$, corresponding to a 23 nm spacing, which agrees well with SAXS and TEM results. The peak positions were determined by fitting the primary peaks with a Gaussian profile. The full-width half maximum (FWHM) for the tension-sensing, compression-sensing, and control films were 0.0071483, 0.006766, 0.011644, 0.0082148, respectively. The FWHM of the primary scattering peak in the scattering profile is a good indication of the ordering of the block copolymer. A smaller full-width half maximum is indicative of better ordering. A slower drying condition results in slightly better ordering for both the tQD sample and the control samples. While these differences are apparent, it is not clear how they could be responsible for the disparity in sensing behavior (i.e., compression-sensing or tension-sensing) observed in the two films.

Supplementary Note 3: Detailed Methods and Supplementary Discussion of Valence Force Field and ab Initio Density Functional Theory Computations The atomic structure of CdSe/CdS core-shell tQDs was generated using a "nanostructure generator" software package that can generate nanocrystals of arbitrary shape and size. The CdSe core of 2.8 nm has zinc-blende crystal structure; the four CdS arms are of wurtzite crystal structure with dimensions of 4.2 nm in length and 2 nm in diameter. The lattice constants and the internal lattice parameter are taken from bulk experimental measurements. Dangling bonds of the surface atoms are passivated by pseudo-hydrogen atoms, with fractional nucleic and electronic charges, to model an ideal passivation. Overall the system contains 4,245 atoms, which is significantly larger than what direct DFT calculations can perform. Therefore, we employ multilevel divide-and-conquer computations. First, the atomistic valence force field (VFF) method is used to relax the atomic positions. Second, the total charge density of the tQD is generated by assembling of atomic charge motifs using the charge patching method (CPM). It has been shown that the CPM can yield essentially the same QD charge density as a self-consistent DFT calculation. Third, the total electron potential is generated from the charge density using the PEtot computational package. Fourth, the band-edge eigenstates are solved using the folded spectrum method, which allows calculations of the band edge eigenstates with a computational effort that scales linearly with the size of the nanoparticle. The resulting single particle eigenenergies have a typical error of 20 meV compared to direct LDA calculations, and the eigenenergy splittings within valence band and conduction band have typical errors of just 5 meV. Thus the current calculations have almost the same accuracy as direct local density approximation (LDA) calculations. We have used plane-wave basis sets and norm-conserving pseudopotentials with a plane-wave cutoff of 35 Ryd. Spin-orbit interaction is included in the single particle Schrodinger equation. In order to check the applicability of our multilevel computational strategy for deformations, we performed a test using bulk CdSe.

The optimized lattice constant for the CdSe zincblende structure using our VFF method is 6.081 Å. Our calculated Poisson's ratio of 0.37 is in agreement with the experimental value of 0.4 and our calculated deformation potential of −3.21 eV is in agreement with the experimental value of −3 eV.

The constructed CdSe/CdS core-shell tetrapod has a band gap of 1.698 eV, close to the experimental band gap of 1.9 eV. Supplementary FIG. 4 shows charge density distributions for the frontier bands of the tQD. Valence band maximum (VBM) and conduction band minimum (CBM) are localized in the CdSe core. This core-localization indicates type-I band alignment in the modelled tQD, which is in agreement with previous experimental results. Lower valence band levels (VBM-1, VBM-2, etc) are also localized in the CdSe core, because the 4p (Se)-orbitals have major contribution to CdSe valence band and selenium is less electronegative then sulfur (the sulfur levels are much lower).

Cd-orbitals have a major contribution to the conduction band in both CdSe and CdS bulk structures. Therefore, the conduction band levels in CdSe core and CdS arms are energetically close: core-localized CBM and arm-localized CBM+1 are separated by only 0.185 eV. Moreover, the CdSe core and CdS arms energy levels eventually mix at higher conduction band levels (CBM+4 and CBM+5) (see FIG. 9). The shapes of the conduction band charge densities are similar to previous calculations for CdSe tQDs. Additionally, the CBM partially penetrates in the arms near the core-arm interface (see FIG. 9).

Since we are applying tensile strain to the polymer, we expect that the tQDs will also experience tensile strain. Therefore, we applied 2.5% tensile strain to the tQD; two of the tQD arms are pulled in one direction while other two arms in the opposite direction. The arm ends are fixed along the deformation axis, while all the other coordinates are relaxed using VFF. The distribution of the local deformation at each atom site (the volume change around each atom) has complex behavior: the deformed tQD shows regions of both tension and compression. Two CdS arms pulled in opposite directions will stretch the region of the CdSe core between them. On the other hand, under tensile strain, the tQD has two pairs of arms that are pulled in the same direction that compress the region of the CdSe core between them like scissors. In case of compressive strain, the situation is the opposite; two arms compress the CdSe core if we push arms in opposite directions and arms pushed in the same strain the joint between them. As a result, a tQD with fixed ends always has regions of both compression and tension simultaneously.

Since the two above described tQD deformations create regions of local tension, the tQD shows a red-shift for both deformations for full VFF relaxation. This is because the region of local tension has the lowest band-gap. At the atomic level, if the distance between two interacting atoms decreases then the gap between their occupied and unoccupied electronic levels increases, if the distance increases the energy gap reduces. The same is applicable to local volumetric deformation around each atom site; local compression increases the energy gap between occupied and unoccupied levels of the atom, while local tension decreases the atomic energy gap. Therefore, when the tetrapod has significant regions of local tension, its band gap decreases (i.e., red-shifts). The calculated band gaps show a small red-shift (see Table 1) for the tetrapod under both tension and compression regimes for the case of full VFF relaxation.

However, for certain experimental nanocomposite processing conditions, (i.e., slow-drying of the solvent-cast polymer film), tQDs show a bandgap increase (i.e., blue-shift) in response to deformation. From the local deformation point of view, this blue-shift suggests that the atoms of the CdSe core, which determine the VBM and CBM, are experiencing net volumetric compression.

In addition to the 2.5% uniaxial and hydrostatic distortions, we also examined the effect of tQD structural twisting, which may appear in a polymer matrix under tensile deformation. In cylindrical coordinates, the twisting deformation implies rotation of each atom around the center axis r by an angle ϕ varying linearly between −2.5% and 2.5% of a full rotation with respect to the tQD center (FIG. 5), such that ϕ(i)=(r(i)−r(0))*a, where ϕ(i) and r(i) are rotation and r coordinate of i-th atom, r(0) radial coordinate of the tQD centre and a=2.352 deg/nm. As with the linear distortions, the ends of the arms are fixed during the VFF relaxation.

While the twisting induces regions of compression at the base of the tQD arms in the direction of rotation, it also produces regions under tension between the opposing pairs of arms. The final tQD structure has a small bandgap red-shift of 17 meV.

Supplementary Note 4: Finite Element Analysis of tQD Core Strains

The determination of the strain state of the CdSe cores in the tQDs is a three scale problem. In the experimental setup we take the loading axis to be the direction e∈R³. Thus at the macroscopic scale, a uniaxial stress state σ=σe⊗e is applied to the sample which behaves in a quasi-incompressible fashion. This generates a state of strain $\varepsilon_A$ in the tQD aggregates at the microscale. Lastly, this strain state induces the nanoscale strain $\varepsilon_C$ of the cores. A simple (hand) solution to the determination of the core strain state is to generate a Mori-Tanaka estimate for $\langle \varepsilon_A \rangle$, the volume average strain in the aggregates. This strain could then be used within a second Mori-Tanaka computation to determine $\langle \varepsilon_C \rangle$, the volume average strain in the cores—issues of self-consistency being observed. Under the assumption of spherical aggregates and cores, the only practical case, this results in a determination that uniaxial tension only generates positive volumetric strains, tr[$\langle \varepsilon_C \rangle$]>0. There is no possibility to induce negative volumetric strains. The failure of the nested Mori-Tanaka methodology to give the possibility of negative volumetric strains is related to the simplifying geometric assumptions in the analysis.

In order to obtain a better estimation, one needs to more fully account for the local geometry of the tQDs. To that end, we utilize a two dimensional plane stress idealization of the system and focus directly on the aggregate.

Due to the random nature of aggregate configurations all computations are performed on ensembles of tQDs. The central question that we explore is under what conditions is it possible to impose a mean aggregate strain $\langle\varepsilon_A\rangle$, which is compatible with macroscopic uniaxial tension, and find that the ensemble average of the volumetric strain of the cores be negative, tr$[\langle\varepsilon_C\rangle]<0$. For the simulations, we impose $\langle\varepsilon_A\rangle\approx 10^{-3}\text{e}\otimes\text{e}-5\times 10^{-4}(1-\text{e}\otimes\text{e})$, where 1 is the identity tensor. As the computation is two dimensional plane stress, the normal strain in the e direction is imposed as is the transverse strain in the plane. The out of plane strain is weakly imposed via the plane stress condition, hence the approximate equals sign. This strain is imposed on a square unit cell of varying dimensions (see below) with periodic boundary conditions. The cell contains randomly placed tQDs for varying numbers (see below). For each realization, the deformation of the unit cell is determined by solving the equations of linear elasticity. From this solution the average strain in the cores within the unit cell is determined.

For the computations, we utilize a regular finite element mesh with mixed bi-quadratic elements (BB-stable Q2P1 elements). The mesh pitch is held constant at 0.15 nm. The unit cell is square with edge dimension L=60+(3/10)n nm, n∈(0,20,40,60). Varying n allows us to vary the 2D packing density of the tQDs. Within each unit cell we place 1, 2, 3 or 4 tQDs at random locations permitting overlaps and periodic imaging across the unit cell edges. The material properties of the finite elements are adjusted according to the randomly chosen center point locations of the tQDs. All elements with a radius of 2 nm of the center point are flagged as CdSe. All elements within a rectangle of width 5.5 nm and length 22 nm from the center point are flagged as CdS (unless they are already flagged as CdSe). This occurs for the rectangle oriented at 0, 120, and 240 degrees. The result is a voxel representation of the geometry. The jagged edges do not appreciably effect the results since we process all data by averaging.

The CdSe core has a zinc-blende structure (space group F43m) with anisotropic elastic constants. Given the limitations of our actual knowledge of the precise state of the system, we employ isotropic elastic constants for the CdSe by projecting the full 4th order elasticity tensor onto the space of isotropic elasticity tensors, viz., $\|C-C^{iso}\|\to\min$. This results in a Young's modulus of 44.6 GPa and a Poisson's ratio of 0.334. The CdS has a wurzite structure (space group P6$_3$mc) with anisotropic elastic constants. The isotropic projection of these properties results in a Young's modulus of 48.3 GPa and a Poisson's ratio of 0.349. For the matrix material we use a Young's modulus of 1.00 MPa and a Poisson's ratio of 0.490.

We identify the ensembles by the number of tQDs in the unit cell and the packing density parameter n. For each ensemble, we consider 200 random realizations. For each realization we apply $\langle\varepsilon_A\rangle\approx 10^{-3}\text{e}\otimes\text{e}-5\times 10^{-4}(1-\text{e}\otimes\text{e})$ and solve the elasticity problem with periodic boundary conditions; depending on the packing density parameter, each computation involves 322 K to 543 K degrees of freedom. Then we average the strain tensor over the cores to determine $\langle\varepsilon_C\rangle$. The algebraic sign of the trace of this quantity indicates if the average core in the realization has a net volume decrease or increase. This process is repeated for each realization drawn from the ensemble. The result is a sequence of 200 values for each ensemble from which we compute the probability that the cores will be in compression in the ensemble. Error bars on the probability values were computed using standard estimates based on the law of large numbers as well MATLAB's bias corrected bootstrap method; both methodologies resulted in equivalent 95 percent confidence levels. The figure in the main part of the paper reports the bootstrapped confidence intervals which are slightly asymmetric. It is also remarked that the ratio of the average pressure in the cores to the mean unit cell stress in the direction of the load gives a substantial enhancement of core stress, up to a few orders of magnitude, similar to that seen experimentally. Future work will more precisely study and statistically assess these substantial enhancements.

Supplementary Note 5: the tQD can Potentially Readily be Used for in-Service Applications A low excitation flux of <2.5e-3 W/cm$^2$ is sufficient to get good signal for tQD stress detection. The excitation flux and detection resolution necessary to detect stress-induced photoluminescence emission maximum shifts from tQDs embedded in structural polymers in service could be achievable with laser pointers and commercially available low-cost portable spectrometers.

What is claimed is:

1. A nanocomposite comprising:
a polymer film comprising a polymer; and
a plurality of fluorescent tetrapod nanocrystals disposed in the polymer film, the fluorescent tetrapod nanocrystals comprising tetrapod quantum dots (tQDs), the plurality of fluorescent tetrapod nanocrystals forming aggregates, and a volume ratio of the tQDs to the polymer defined by a tQD aggregate fill fraction or a packing density in the aggregates being approximately 40%-50%±5% for a compression-sensing nanocomposite and 20%-30%±2% for a tension-sensing nanocomposite.

2. The nanocomposite of claim 1, wherein a volume ratio of the tQDs to the polymer defined by a tQD aggregate fill fraction or a packing density in the aggregates is approximately 50%±5% for a compression-sensing nanocomposite and 25%±2% for a tension-sensing nanocomposite.

3. The nanocomposite of claim 1, wherein the tQDs are approximately a factor of two farther apart in a tension-sensing aggregate than in a compression-sensing aggregate, and wherein the tension-sensing aggregate has approximately a factor of two times more polymer inside of the tension-sensing aggregate in terms of small-scale inter-tQD regions.

4. The nanocomposite of claim 1, wherein a tensile stress applied to densely-packed tQDs in the polymer results in a blue-shift of a tQD photoluminescence emission maximum due to a uniform compression of tQD cores, and wherein a tensile stress applied to loosely-packed tQDs in the polymer results in a red-shift of a tQD photoluminescence emission maximum due to a net core tension.

5. The nanocomposite of claim 1, wherein the aggregates for a compression-sensing nanocomposite exhibit a higher energy blue-shift of a tQD photoluminescence emission maximum under tensile stress due to a compression of tQD cores.

6. The nanocomposite of claim 1, wherein the aggregates for a tension-sensing nanocomposite exhibit a lower energy red-shift of a tQD photoluminescence emission maximum under tensile stress due to a tension of tQD cores.

7. The nanocomposite of claim 1, wherein a tQD comprises a cadmium selenide-cadmium sulfide (CdSe—CdS) core/shell tQD.

8. The nanocomposite of claim 7, wherein a tQD has an arm length of approximately 26 nanometers ±3 nanometers.

9. The nanocomposite of claim 7, wherein a zinc-blende CdSe core has a diameter of approximately 2.8 nanometers.

10. The nanocomposite of claim 7, wherein a wurtzite CdS arm is approximately 4.2 nanometers in length and 1.9 nanometers in diameter.

11. The nanocomposite of claim 7, wherein the CdSe—CdS core/shell tQD contains approximately 4245 atoms, and wherein the CdSe—CdS core/shell tQD has a chemical formula $Cd_{272}Se_{297}/Cd_{1132}S_{1116}$.

12. The nanocomposite of claim 1, wherein the polymer comprises a block copolymer.

13. The nanocomposite of claim 12, wherein the block copolymer comprises poly(styrene-ethylene-butylene-styrene) (SEBS).

14. The nanocomposite of claim 13, wherein the SEBS comprises approximately 60% polystyrene (PS) and 40% poly(ethylene-butylene) (P-EB).

15. A nanocomposite comprising:
a polymer film comprising a polymer; and
a plurality of fluorescent tetrapod nanocrystals disposed in the polymer film, the fluorescent tetrapod nanocrystals comprising tetrapod quantum dots (tQDs), the plurality of fluorescent tetrapod nanocrystals forming aggregates, a tensile stress applied to densely-packed tQDs in the polymer resulting in a blue-shift of a tQD photoluminescence emission maximum due to a uniform compression of tQD cores, a tensile stress applied to loosely-packed tQDs in the polymer resulting in a red-shift of a tQD photoluminescence emission maximum due to a net core tension, the tQDs being approximately a factor of two farther apart in a tension-sensing aggregate than in a compression-sensing aggregate, and the tension-sensing aggregate having approximately a factor of two times more polymer inside of the tension-sensing aggregate in terms of small-scale inter-tQD regions.

16. The nanocomposite of claim 15, wherein a volume ratio of the tQDs to the polymer defined by a tQD aggregate fill fraction or a packing density in the aggregates is approximately 40%-50%±5% for a compression-sensing nanocomposite and 20%-30%±2% for a tension-sensing nanocomposite.

17. A nanocomposite comprising:
a polymer film comprising a polymer; and
a plurality of fluorescent tetrapod nanocrystals disposed in the polymer film, the fluorescent tetrapod nanocrystals comprising tetrapod quantum dots (tQDs), a tQD comprising a cadmium selenide-cadmium sulfide (CdSe—CdS) core/shell tQD, a wurtzite CdS arm being approximately 4.2 nanometers in length and 1.9 nanometers in diameter, and the plurality of fluorescent tetrapod nanocrystals forming aggregates.

18. The nanocomposite of claim 17, wherein the tQDs are approximately a factor of two farther apart in a tension-sensing aggregate than in a compression-sensing aggregate, and wherein the tension-sensing aggregate has approximately a factor of two times more polymer inside of the tension-sensing aggregate in terms of small-scale inter-tQD regions.

19. The nanocomposite of claim 17, wherein a tensile stress applied to densely-packed tQDs in the polymer results in a blue-shift of a tQD photoluminescence emission maximum due to a uniform compression of tQD cores, and wherein a tensile stress applied to loosely-packed tQDs in the polymer results in a red-shift of a tQD photoluminescence emission maximum due to a net core tension.

20. The nanocomposite of claim 17, wherein the CdSe—CdS core/shell tQD contains approximately 4245 atoms, and wherein the CdSe—CdS core/shell tQD has a chemical formula $Cd_{272}Se_{297}/Cd_{1132}S_{1116}$.

* * * * *